United States Patent [19]
Honeycutt et al.

[11] Patent Number: 6,010,444
[45] Date of Patent: Jan. 4, 2000

[54] INFECTIOUS WASTE CONTAINMENT SYSTEM

[75] Inventors: Travis W. Honeycutt, Gainesville; Baosheng Lee, Duluth; Dong Dai, Lawrenceville; Robert S. Woody, Hiram, all of Ga.

[73] Assignee: Isolyser Company, Inc., Norcross, Ga.

[21] Appl. No.: 08/926,252

[22] Filed: Sep. 5, 1997

[51] Int. Cl.[7] ............................................. B09B 3/00
[52] U.S. Cl. .................... 588/255; 588/258; 588/259; 206/365; 206/366; 428/35.7; 422/900
[58] Field of Search .................................. 588/249, 255, 588/258, 259, 901; 206/364, 365, 366; 422/900; 428/34.1, 35.7

[56] References Cited

U.S. PATENT DOCUMENTS

| | | |
|---|---|---|
| 2,602,042 | 7/1952 | Abbott . |
| 2,772,999 | 12/1956 | Masci et al. . |
| 2,773,000 | 12/1956 | Masci et al. . |
| 3,292,776 | 12/1966 | Penn . |
| 3,547,747 | 12/1970 | Roberts . |
| 3,638,709 | 2/1972 | Brown, Jr. et al. . |
| 3,653,567 | 4/1972 | Selvaggio . |
| 3,722,599 | 3/1973 | Robertson et al. . |
| 3,897,579 | 7/1975 | Weinstein . |
| 3,921,801 | 11/1975 | Sway . |
| 3,999,653 | 12/1976 | Haigh et al. . |
| 4,058,124 | 11/1977 | Yen et al. . |
| 4,134,929 | 1/1979 | Stoakley et al. . |
| 4,139,693 | 2/1979 | Schoenberg . |
| 4,170,585 | 10/1979 | Motegi et al. . |
| 4,171,226 | 10/1979 | Hesselgren .............................. 588/258 |
| 4,171,416 | 10/1979 | Motegi et al. . |
| 4,320,157 | 3/1982 | von Hagens . |
| 4,410,086 | 10/1983 | Simpson . |
| 4,444,933 | 4/1984 | Columbus et al. . |
| 4,454,055 | 6/1984 | Richman et al. . |
| 4,466,888 | 8/1984 | Verkaart . |
| 4,477,607 | 10/1984 | Litke . |
| 4,520,926 | 6/1985 | Nelson . |
| 4,600,112 | 7/1986 | Shillington et al. . |
| 4,600,610 | 7/1986 | Hrovat et al. ............................... 428/2 |
| 4,601,880 | 7/1986 | Wong et al. ............................... 422/28 |
| 4,650,086 | 3/1987 | Morrison, Jr. ........................... 206/524 |
| 4,662,516 | 5/1987 | Baker, Sr. et al. ...................... 206/366 |
| 4,715,498 | 12/1987 | Hanifl ..................................... 206/366 |
| 4,722,472 | 2/1988 | Bruno ..................................... 206/366 |
| 4,759,445 | 7/1988 | McVay ................................... 206/524 |
| 4,816,307 | 3/1989 | Honeycutt . |
| 4,830,913 | 5/1989 | Ortmans et al. ........................... 428/34 |
| 4,833,165 | 5/1989 | Louderback ......................... 422/28 X |
| 4,842,597 | 6/1989 | Brook ..................................... 604/363 |
| 4,883,478 | 11/1989 | Lerailler ............................. 604/364 X |
| 4,900,500 | 2/1990 | Honeycutt . |
| 4,919,569 | 4/1990 | Wittenzelliner ......................... 405/128 |
| 5,152,394 | 10/1992 | Hughes .................................. 206/366 |
| 5,172,808 | 12/1992 | Bruno ..................................... 206/366 |
| 5,271,892 | 12/1993 | Hanson et al. ...................... 206/366 X |
| 5,281,391 | 1/1994 | Hanson et al. ...................... 206/366 X |
| 5,322,165 | 6/1994 | Melker et al. .......................... 206/366 |
| 5,372,252 | 12/1994 | Alexander .......................... 206/366 X |
| 5,663,447 | 9/1997 | Honeycutt .............................. 588/205 |
| 5,674,175 | 10/1997 | Bailey .................................... 588/255 |
| 5,707,173 | 1/1998 | Cottone et al. ..................... 588/259 X |

FOREIGN PATENT DOCUMENTS 2229717  11/1992  United Kingdom .

OTHER PUBLICATIONS

"Infection Prevention Products" Published in Biomedical Business International, vol. IX No.13. Jul. 10, 1986, pp. 128 & 129.

*Primary Examiner*—George Suchfield
*Attorney, Agent, or Firm*—Needle & Rosenberg, P.C.

[57] ABSTRACT

A method for containing potentially infectious devices. The potentially infectious devices are deposited in a container which contains a monomer, a reducing agent and water. An oxidizing agent is later added to cause polymerization of the monomer to immobilize the devices, and to act as a disinfecting agent due in large part to the exothermic nature of the reaction. In an alternate embodiment, the composition contains a monomer, a thickener and water. Before use, this solution is admixed with an oxidizing and reducing agent and the thickened solution is poured into a container having disposed therein potentially infectious devices. Related methods, kits, devices, and compositions are also disclosed.

20 Claims, 1 Drawing Sheet

INFECTIOUS WASTE CONTAINMENT SYSTEM

BACKGROUND OF THE INVENTION

I. Field of the Invention

The present invention deals with infectious waste disposal systems and particularly those which are designed for use in hospitals and other environments in which medical practitioners routinely contaminate a host of devices such as needles, syringes, tubing and scalpels with blood and other bodily fluids which then require disposal.

II. Background of the Invention

In hospitals, clinics and other environments in which ill patients are routinely examined and treated, medical practitioners contaminate a host of devices such as needles, syringes, tubing and scalpels with blood and other bodily fluids. This is often done when feeding patients intravenously, drawing bloods, vaccinating and otherwise inoculating patients against various diseases. Quite often, patients' bodily fluids are infected with pathogenic bacteria, viruses, fungi and other matter. The potential source of pathogenicity has been acute with the knowledge and identification of certain pathogens, such as hepatitis B and the AIDS virus, among other deadly and infectious materials.

These pathogenetic materials are potentially a source of infection for doctors, nurses, aids, orderlies, technicians and even visitors to the hospital or clinic, as well as to the patients themselves. The various devices infected must thus be contained and/or destroyed.

Currently, infectious waste, called "sharps", is generally disposed of by insertion of the infected material into a passive hard plastic container. These containers are then removed by housekeeping personnel and sent to a site for bagging and storage. After bagging, the containers are often stored or removed to yet another site for disinfection. Even when closed, locked and bagged, the containers are not airtight, and thus can potentially spill and contaminate the atmosphere. Handling of the waste containers often results in infected needles penetrating storage containers, thus providing a further potentially dangerous condition for housekeeping personnel.

Following sterilization, the contaminated material is often removed to another location for incineration, storage or disposal in a landfill. Thereafter, the waste disposal containers resemble, and are often referred to as, "porcupines" because the often used plastic containers shrink around the needles and other devices when heated in an autoclave or similar device, resulting in needle exposure through the sidewalls of the containers. In this condition, the containers are indeed quite dangerous to handle, whether or not they remain the housing for infectious devices.

One of the most serious deficiencies with current disposal methods is that they do not prevent the aerosoling or spilling of infectious materials into the ambient atmosphere, thus potentially causing the spread of infectious germs, bacteria, fungi and viral fragments. Current containers are not airtight, even when they are eventually closed and locked. As such, there remains outstanding potential for cross infection by vectors such as flies, rodents, etc., and undesirable odor is a further problem.

It is thus an object of the present invention to provide a superior means for containing potential infectious devices which overcomes the difficulties recited above.

This and further objects of the present invention will be more fully appreciated when considering the following disclosure.

SUMMARY OF THE INVENTION

In its broadest sense, the present invention involves compositions, devices, kits and methods for disinfecting and containing potentially infectious devices. The methods comprises depositing the potentially infectious devices in a container to which is added a sufficient quantity of an acrylic or acrylamide monomer-containing composition which includes, for example, acrylates which are esters of acrylic acid and their derivatives, methacrylic acids and their derivatives, and acrylamides and their derivatives. The composition also contains a reducing agent. The composition is included in a sharps container to a level that would fully, or at least partially, envelope any potentially infectious devices deposited into the container. The acrylic monomer-containing composition is then hardened through polymerization of the aqueous acrylic monomer via the addition of an oxidizing agent. As a further benefit, the polymerization is sufficiently exothermic such that immobilization and disinfection, or at least neutralization, of the potentially infectious biological organisms occurs. The potentially infectious materials are thus contained and rendered essentially safe. For disinfection, it is desirable that the peak temperature during polymerization reach 70° C.

In another embodiment, the invention provides a method not suffering from the splashing or aerosoling issues mentioned above. In this method, the acrylic monomer or acrylamide monomer is admixed with a thickener. The resulting viscous composition is added to a sharps container or other container holding infectious materials. The composition can be composed with either the reducing agent or oxidizing agent therein. The activating, respective, oxidizing agent (or reducing agent) may be mixed with the composition just prior to use. The composition is deposited into the container, without splash risk due to the viscosity and without the risk of lighter infectious material floating to the top of the solution. The solution polymerizes in situ in the container, thereby neutralizing the dangerous materials, similar to the description above.

Moreover, the present invention provides a composition for containing potentially infectious devices, comprising N-methylolacrylamide, a tertiary amine reducing agent admixed with the N-methylolacrylamide, and water. The invention also provides a composition for containing potentially infectious devices, comprising N-methylolacrylamide, a thickener admixed with the N-methylolacrylamide, and water.

In a further embodiment, the invention provides a method for containing potentially infectious items, the method comprising providing a container having therein a composition comprising an acrylic or acrylamide monomer, a reducing agent admixed with the acrylic or acrylamide monomer, and water, then depositing one or more potentially infectious items into the container, and, at a predetermined time, causing polymerization of the composition by admixing with the composition in the container an oxidizing agent.

In a further embodiment, the present invention provides a method for containing potentially infectious items, the method comprising providing a container having therein one or more potentially infectious items, depositing into the container the composition of the invention, and, at a predetermined time, causing polymerization of the composition by admixing with the composition in the container an oxidizing agent.

In still a further embodiment, the invention provides a kit for containing potentially infectious items, the kit comprising an oxidizing agent and a container having disposed therein a composition comprising an acrylic or acrylamide monomer, a reducing agent admixed with the acrylic or acrylamide monomer, and water. The invention also provides a kit for containing potentially infectious items, the kit comprising an oxidizing agent, a reducing agent, and a container having disposed therein a composition comprising an acrylic or acrylamide monomer, a thickener, and water.

Moreover, the present invention also provides a device for containing potentially infectious items, the device comprising a container resistant to puncture by sharps and having disposed therein a composition comprising an acrylic or acrylamide monomer, a reducing agent admixed with the acrylic or acrylamide monomer, and water.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE PREFERRED EMBODIMENTS

Figure 1:
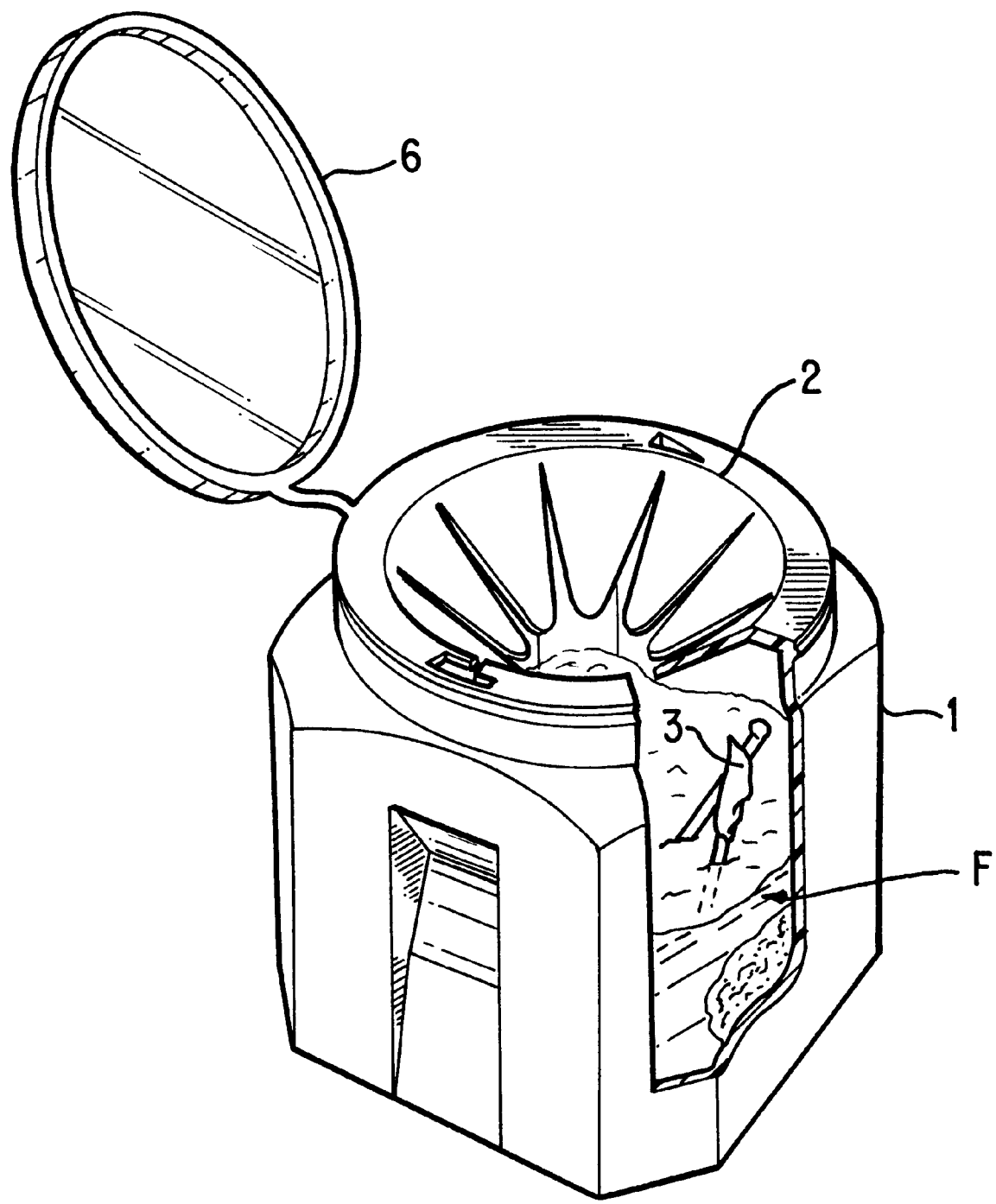
FIG. 1 shows a perspective view of a container useful for practicing the present invention.

The present invention may be understood more readily by reference to the following detailed description of preferred embodiments of the invention and the FIGURE.

Before the present articles and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains.

In particular, the present invention provides a composition for containing potentially infectious devices. This composition includes N-methylolacrylamide monomer, a tertiary amine reducing agent admixed with the N-methylolacrylamide, and water. In addition, antifoaming agents, stabilizers (such as chelating agents), and disinfectants can be added to the basic composition or the other compositions of this invention. One preferred reducing agent is tetramethylethylenediamine. In a further embodiment, the composition can contain a thickener, as described below.

During activation, a further composition is formed, one also comprising an oxidizing agent.

In an alternate embodiment, the present invention provides a further composition for containing potentially infectious devices. This composition includes N-methylolacrylamide, a thickener admixed with the N-methylolacrylamide, and water. As with the previous composition, additional ingredients such as antifoaming agents, stabilizers, and disinfectants are also included. In another embodiment, for instance just prior to use, this composition is extended to contain a reducing agent and an oxidizing agent. Suitable reducing agents include tertiary amines.

In addition to these compositions, the invention provides new methods for containing potentially infectious items. One method involves providing a container having therein a composition comprising an acrylic or acrylamide monomer, a reducing agent admixed with the acrylic or acrylamide monomer, and water, then depositing one or more potentially infectious items into the container, and, at a predetermined time, causing polymerization of the composition by admixing with the composition in the container an oxidizing agent. The compositions useful for this method can contain the additives discussed elsewhere herein. A further method is provides for containing potentially infectious items, the method comprising providing a container having therein one or more potentially infectious items, depositing into the container the composition of the monomer and the reducing agent and, at a predetermined time, causing polymerization of the composition by admixing with the composition in the container an oxidizing agent.

Finally, the invention provides kits and devices for containing potentially infectious items. Such kits or devices comprise an oxidizing agent and a container having disposed therein a composition comprising an acrylic or acrylamide monomer, a reducing agent admixed with the acrylic or acrylamide monomer, and water. Similarly, alternate devices can be made where the monomer is combined with a thickener to increase the viscosity of the composition. In particular, the kit comprises an oxidizing agent, a reducing agent, and a container having disposed therein a composition comprising an acrylic or acrylamide monomer, a thickener, and water.

The present method involves the entrapment, anchoring or immobilization of contaminated and/or infected "sharps" and their aerosol through the use of a container and solidifying agent at the point of disposal. In one embodiment, the container has therein a composition including an acrylic or acrylamide monomer, a reducing agent, and water. Suitable reducing agents are those general known in the redox polymerization art, including tertiary amines in general. Other suitable reducing agents include tetramethylethylenediamine ("TMEDA"), DABCO® (Aldrich St. Louis Mo.), aniline, sodium sulfate, or pyridine. In a preferred embodiment, the reducing agent is present from about 0.01% to about 10.0%, by weight, of the composition, more particularly about 0.25% by weight of the composition. In general, the monomer should be water-soluble and capable of forming a homogenous gel with water.

The container contains enough of this material to cover, at least partially, the infected "sharps" material. After the container is deemed full, the user simply adds an oxidizing agent to the composition in the container, which causes an exothermic polymerization to occur that turns the composition into a solid block of plastic. The liquid can contain additional biocides or disinfectants and naturally produces biocidal activity and sanitizing heat during the course of the reaction, which is decidedly exothermic.

The preferred solidifying liquid is an acrylic based monomer-containing composition which includes acrylic acids and their derivatives, methacrylic acids and their derivatives, as well as acrylamides and their derivatives. The aqueous/acrylic monomer-containing composition incorporates the potentially infectious fluids into their polymer matrices as the polymerization proceeds. The acrylic acid complexes amino acids and proteins which are known constituents of blood and bodily fluids, thus immobilizing and containing these fluids. As such, acrylic and acrylic ester monomer-containing compositions provide an ideal material to contain potentially infectious devices which have been infected with bodily fluids. It is hypothesized that the monomer containing composition reacts through a polymerization cascade and causes a grafting reaction to take place whereby the organic matter in the infectious waste is thereby "caught up", bound or covalently reacted with the monomer and thus becomes a part of the "thermoset" matrix.

Suitable acrylic monomers include N-methylolacrylamide ("NMA"), acrylic acids, acrylamides, acrylic esters, and acrylonitriles. In a preferred embodiment, the monomer comprises about 20 to 90%, by weight, more preferably about 55% of the composition.

The preferred immobilizing composition comprises an acrylic monomer having the following structure:

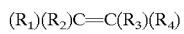

wherein:

$R_1$ is —COOH; —COOR$_5$; CONHOH; CONHCH$_2$OH; or CONH$_2$;

$R_2$ is H; CH$_3$; CH$_3$CH$_2$; or CN;

$R_3$ and $R_4$ are, independently, H; CH$_3$; CH$_3$CH$_2$; or halogen; and $R_5$ is an alkyl of from 1 to 12 carbon atoms, preferably CH$_3$; an alkoxyalkyl such as ethoxyethyl; a hydroxyalkyl such as a hydroxyethyl; an acrylamide or its bis product, such as methylene-bis-acrylamide.

For the purposes of the present invention, the polymerization is via the free radical route. To enhance shelf life, it is preferable that a free radical scavenger be included in the composition. Such scavengers include hydroquinone, monoethyl ether of hydroquinone, butylated hydroxyanisole, butylated hydroxytoluene and t-butyl hydroquinone. Hydroquinone or its monoethyl ether is the preferred free radical scavenger for use herein. It is further contemplated that the monomer-containing compositions also include a "promoter", such as ferrous or cuprous salts, and in the case of "redox" catalyst systems, a reducing agent. These are materials such as sodium-meta-bisulfite, isoascorbic acid, sodium sulfite or tertiary amines such as N,N-dimethyltoluedine or N,N-dihydroxyethyl-paratoluedine.

Also included as possible preferred expedients in the system are aldehydes such as formaldehyde and glutaraldehyde and phenols and its derivatives such as orthophenylphenol and its sodium salt as disinfectants.

While an "oil" based or hydrophobic system may be feasible, a more preferred system is one which is aqueous based. The aqueous base systems are preferred for land-fill considerations as aqueous based materials are easier to contain in a land-fill area due to various legal restrictions on burying "organic" materials.

Viscous materials provide several benefits. In particular, splashing is reduced, if not eliminated. Moreover, the system does not permit certain objects, such as needles, to float to the top of the solution before polymerization is completed. Finally, a more viscous solution, when used with a third party container, is less likely to leak in the event that the container has a puncture of some kind.

It is further contemplated that in practicing the present invention, an initiating agent or catalyst be employed to promote the polymerization of the monomer. Preferably, the catalyst consists of a persulfate (such as ammonium persulfate—APS), peroxide or perborate, alone, or in a solvent or plasticizer such as a detergent, soap or surfactant.

The preferred embodiments of the above-described articles and methods are set forth in the following examples. Other features of the invention will become apparent from the following examples, which are for illustrative purposes only and are not intended as a limitation upon the present invention.

As distinguished from prior systems, referring now to FIG. 1, the present invention provides a ready-to-use device, in one embodiment, of the sharps container 1, the prepolymer and the reducing agent (together F). One of skill in the art would recognize that an oxidizing agent could, instead, be included in the initial composition in the container. However, this is somewhat less preferable because the oxidizing agent could degrade the monomer, for example. In addition, initiation of the polymerization could occur if the monomer or some other component were to have reducing agent properties. When using an oxidizing agent in solution with the monomer, it is preferred to use a less strong oxidizing agent, to minimize the amount of premature polymerization. Examples of such agents include, but are not limited to, FeCl$_3$, H$_2$O$_2$, NaClO, and NaClO$_3$. Stronger oxidizing agents (suitable for use in the alternate embodiment where the reducing agent is in solution and the oxidizing agent is added afterward) include, but are not limited to, KClO$_4$, KMnO$_4$, and OsO$_4$. One of ordinary skill in the art could choose other oxidizing agents depending upon the particular results desired.

Therefore, focusing on the embodiment where the reducing agent is admixed with the monomer, an oxidizing agent (not shown) is then added to the container 1 when the user determines that the sharps 3 or dangerous materials should be neutralized. For neutralization, the user can simply add the oxidizing agent, close the cap 6 of the container 1 to form a fluid-tight seal (at 2) and agitate the container 1. However, even without closing of the cap 6 and agitation, the polymerization will occur.

In a further embodiment, a viscosity enhanced solution of the prepolymer, a thickener and water can be stored as a separate mixture. Suitable thickeners are generally known to those of skill in the art and include Hydrosafe 80HS. It is preferred that the thickener comprise from 0.01 to 30.0%, by weight, of the composition, preferably about 1.35%.

This mixture can be used to contain sharps or other materials in a preexisting container. The mixture can, optionally, already contain a reducing agent. In one embodiment, before pouring the mixture into the container, an oxidizing agent is added to the composition. It is desirable that the polymerization not occur so rapidly that the user cannot pour the activated composition into the container. In particular, at least about 1 to 5 minutes, or longer, before setting commences has been found desirable. After setting commences, it is desirable that the polymerization occur fairly rapidly, so that the user is not inconvenienced in having to await completion of polymerization. In particular, a polymerization time of less than about 10 minutes is desirable. However, one of skill in the art could easily vary the initiation and polymerization times by varying monomer concentration, reducing agent or oxidizing agent concentration or identity, temperature conditions and agitation conditions.

Of course, additional ingredients could be added to the formulations useful for practicing the invention, for example fillers, and such addition would correspondingly modify the initiation and polymerization times and properties (such as peak temperature).

Alternatively, the mixture with the reducing agent can be added to the container before contacting the solution with the oxidizing agent.

The ingredients of the invention, including the container, can be used to create neutralization kits for rendering safe sharps or other dangerous or infectious materials. The kits include the container and the compositions described above.

Furthermore, the invention provides for new containment devices, which are comprised of the container already holding the compositions of the invention, as also described above.

The following examples are set forth so as to provide those of ordinary skill in the art with a complete disclosure and description of how the compositions and articles claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and is at room temperature, and pressure is at or near atmospheric.

EXAMPLE I

Single Catalyst Sharps Management Solution

| Ingredients | Preferred Percentage | Supplier (if applicable) |
|---|---|---|
| Water | 44.15 | |
| VERSENE ® 100 | 0.20 | Ashland Chemical (Doraville GA) |
| ANTIFOAM 1410 | 0.10 | Ashland Chemical (Doraville GA) |
| NMA 48% | 55.0 | National Starch and Chemical (Salisbury NC) |
| LPHSE | 0.30 | Steris Corp. (St. Louis MO) |
| TMEDA (Reducing Agent) | 0.25 | Aldrich (Milwaukee WI) |
| Catalyst | | |
| APS (Ammonium Persulfate) - Oxidizing agent | | Ashland Chemical (Doraville GA) |

This composition had a starting pH of about 9.88. Using 800 g. of the composition and 0.8 g of catalyst starting at 23° C., the polymerization resulted in a final temperature of 70° C.

EXAMPLE II

Thickened Sharps Management Solution

| Ingredients | Preferred Percentage | Supplier (if applicable) |
|---|---|---|
| Water | 38.05 | |
| VERSENE ® 100 | 0.20 | |
| ANTIFOAM 1410 | 0.10 | |
| NMA 48% | 60.0 | |
| LPHSE | 0.30 | |
| HYDROSAFE 80HS | 1.35 | Stockhausen (Greensboro NC) |
| Catalysts | | |
| APS - Oxidizing agent | | |
| PAROLITE (zinc formaldehyde sulfoxylate) - Reducing agent | | Henkel (Mauldin SC) |

EXAMPLE III

Single Catalyst, Thickened Sharps Management Solution

| Ingredients | Preferred Percentage |
|---|---|
| Water | 37.80 |
| VERSENE ® 100 | 0.20 |
| ANTIFOAM 1410 | 0.10 |
| NMA 48% | 60.0 |
| LPHSE | 0.30 |
| TMEDA (Reducing Agent) | 0.25 |
| HYDROSAFE 80HS | 1.35 |
| Catalysts | |
| APS - Oxidizing agent | |

EXAMPLE IV

The composition of Example I was assayed with and without 10 g. of thickener HYDROSAFE 80HS. In addition, the third column of the table represents the addition of catalyst (APS) to the solution before adding the solution into the container. Finally, the fourth column of the table represents the same assay as Column 3, except using 11 g. Of 80HS.

| Column | 1 | 2 | 3 | 4 |
|---|---|---|---|---|
| Solution | 800 g | 800 g | 800 g | 800 g |
| Thickener | 0 | 10 g | 10 g | 11 g |
| Catalyst | 0.8 g | 0.8 g | 0.8 g | 0.8 g |
| Start Temp. | 23° C. | 23° C. | 23° C. | 23° C. |
| Initiation Time | 5.5 min. | 7 min. | 7.5 min. | 7.5 min. |
| Peak Temp. | 70° C. | 72° C. | 71° C. | 67° C. |
| Temp. Change | 47° C. | 49° C. | 48° C. | 44° C. |
| Time for Temp. Change | 6.5 min. | 8.5 min. | 6.5 min. | 8 min. |

EXAMPLE V

The composition of Example III was assayed for aging. The columns represent various aging periods.

| Column | 1 | 2 | 3 | 4 |
|---|---|---|---|---|
| Age | 1 day | 8 days | 17 days | 23 days |
| Solution | 800 g | 800 g | 800 g | 800 g |
| Catalyst | 0.8 g | 0.8 g | 0.8 g | 0.8 g |
| Start Temp. | 24° C. | 24° C. | 23° C. | 25° C. |
| Initiation Time | 7.5 min. | 8 min. | 8.5 min. | 8 min. |
| Peak Temp. | 80° C. | 79° C. | 79° C. | 81° C. |
| Temp. Change | 56° C. | 55° C. | 56° C. | 56° C. |
| Time for Temp. Change | 8.5 min. | 7.0 min. | 5.5 min. | 5.5 min. |

The data demonstrate that disinfecting temperatures were reached within a fairly rapid period of time and that the efficacy of the composition did not significantly degrade over the aging period.

It is thus an object of the present invention to provide a superior method for containing potential infectious devices which overcomes the difficulties recited above.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A method for containing potentially infectious items, the method comprising:
    a) providing a container having therein a composition comprising:
        i) a water-soluble monomer that polymerizes upon addition of a polymerization initiating agent; and
        ii) water;
    b) depositing one or more potentially infectious items into the container; and
    c) at a predetermined time, causing polymerization of the composition by admixing with the composition in the container the polymerization initiating agent.

2. The method of claim 1, wherein the monomer is an acrylic or acrylamide monomer having admixed therein a reducing agent and wherein the polymerization initiating agent is an oxidizing agent.

3. The method of claim 1, wherein the composition further comprises an antifoaming agent.

4. The method of claim 1, wherein the composition further comprises a stabilizer.

5. The method of claim 1, wherein the composition further comprises a disinfectant.

6. The method of claim 1, wherein the reaction is sufficiently exothermic to achieve a peak temperature of at least 70° C. for a sufficient amount of time to permit disinfection.

7. The method of claim 2, wherein the acrylic or acrylamide monomer comprises N-methylolacrylamide.

8. The method of claim 2, wherein the reducing agent comprises tetramethylethylenediamine.

9. The method of claim 3, wherein the stabilizer is a chelating agent.

10. A method for containing potentially infectious items, the method comprising:
    a) providing a container having therein one or more potentially infectious items;
    b) depositing into the container a composition comprising:
        i) N-methylolacrylamide;
        ii) a thickener admixed with the N-methylolacrylamide;
        iii) water; and
        iv) a reducing agent; and
    c) at a predetermined time, causing polymerization of the composition by admixing with the composition in the container an oxidizing agent.

11. The method of claim 10, further comprising an antifoaming agent.

12. The method of claim 10, further comprising a stabilizer.

13. The method of claim 10, wherein the stabilizer is a chelating agent.

14. The method of claim 10, further comprising a disinfectant.

15. A kit for containing potentially infectious items, the kit comprising an oxidizing agent and a container having disposed therein a composition comprising:
    a) an acrylic or acrylamide monomer;
    b) a reducing agent admixed with the acrylic or acrylamide monomer; and
    c) water.

16. A kit for containing potentially infectious items, the kit comprising a reducing agent and a container having disposed therein a composition comprising:
    a) an acrylic or acrylamide monomer;
    b) an oxidizing agent admixed with the acrylic or acrylamide monomer; and
    c) water.

17. A kit for containing potentially infectious items, the kit comprising an oxidizing agent, a reducing agent, and a container having disposed therein a composition comprising:
    a) an acrylic or acrylamide monomer;
    b) a thickener; and
    c) water.

18. The kit of claim 17, wherein the composition further comprises a reducing agent.

19. A device for containing potentially infectious items, the device comprising a container resistant to puncture by sharps and having disposed therein a composition comprising:
    a) N-methylolacrylamide;
    b) a reducing agent admixed with the N-methylolacrylamide; and
    c) water.

20. A device for containing potentially infectious items, the device comprising a container resistant to puncture by sharps and having disposed therein a composition comprising:

a) N-methylolacrylamide;

b) an oxidizing agent admixed with the N-methylolacrylamide; and c) water.

* * * * *